United States Patent [19]

Polyakov et al.

[11] 4,192,961

[45] Mar. 11, 1980

[54] METHOD AND CATALYST FOR PREPARING STYRENE

[76] Inventors: Sergei A. Polyakov, 3 Sovetskaya ulitsa, 16, kv. 9; Aron L. Shapiro, ulitsa Lensoveta, 50, kv. 29; Viktor J. Gankin, ulitsa Khalturina, 20, kv. 6, all of Leningrad, U.S.S.R.

[21] Appl. No.: 839,348

[22] Filed: Oct. 4, 1977

[51] Int. Cl.² ............................................. C07C 15/00
[52] U.S. Cl. .................................. 585/319; 585/422; 585/510; 252/458
[58] Field of Search ........... 260/669 B, 668 C, 669 R; 252/458

[56] References Cited

U.S. PATENT DOCUMENTS

| | | | |
|---|---|---|---|
| 2,369,281 | 2/1945 | Chaney | 260/669 R |
| 2,954,413 | 9/1960 | Kroeper et al. | 260/668 C |
| 3,062,903 | 11/1962 | Odioso et al. | 260/669 B |
| 3,441,625 | 4/1969 | Bergeron et al. | 260/668 C |
| 3,963,793 | 6/1976 | Weterings | 260/668 C |

*Primary Examiner*—Delbert E. Gantz
*Assistant Examiner*—Joseph A. Boska
*Attorney, Agent, or Firm*—Lackenbach, Lilling & Siegel

[57] ABSTRACT

A method and catalyst for preparing styrene which comprises dehydrodimerization of toluene, followed by conversion of the resulting dehydrodimerization products to styrene. The conversion is conducted in the presence of ethylene using a catalyst consisting of chromium oxide, tungsten oxide and an alkali metal oxide supported by a carrier. The method according to the present invention makes it possible to increase the yield of styrene and simplify the process technology.

1 Claim, No Drawings

METHOD AND CATALYST FOR PREPARING STYRENE

FIELD OF THE INVENTION

The present invention relates to the art of petrochemistry and, more specifically, to a method for preparing styrene.

Styrene is one of most important monomers in the modern industry of rubber and plastics. The world production of styrene is now over 6 mln. tons.

BACKGROUND OF THE INVENTION

Known in the art is a method for preparing styrene from toluene which comprises passing a mixture of toluene, air and water over bismuth oxide at a temperature within the range of from 500° to 580° C. to produce a mixture of dibenzyl and stilbene. The dehydrodimerization products (dibenzyl and stilbene) are subjected to a catalytic hydrocracking to ethylbenzene and benzene. Thus, in hydrocracking performed at a temperature of 450° C. under a pressure of 28 atm on a catalyst containing 16% by weight of $Cr_2O_3$ on alumosilicate, conversion of dehydrodimerization products is 26%, the yield of ethylbenzene is 31.8% by weight. The resulting ethylbenzene is subjected to dehydration to styrene.

Also known in the art is a process for producing styrene consisting in that dibenzyl resulting from dehydrodimerization of toluene is subjected to conversion directly to styrene and benzene. Thus, in the presence of a catalyst containing, percent by weight: $SiO_2$ 73; $Al_2O_3$—17; $Fe_2O_3$—1.5; $MgO$—4; $CaO$—2, at the temperature of 550° C. and space velocity of 18.3 $hr^{-1}$, conversion of dibenzyl is 18.7%; the yield of styrene is 22.4% by weight.

Upon dehydrodimerization of toluene there is formed a mixture of dibenzyl and stilbene, wherein the dehydrodimerization products can be subjected to conversion to styrene only after a preliminary hydrogenation of stilbene.

The prior art methods have certain disadvantages residing in a low yield of styrene and multi-stage character of the process.

SUMMARY OF THE INVENTION

It is an object of the present invention to increase the desired product yield and simplify the process technology.

This and other objects of the present invention are accomplished by a method for preparing styrene by dehydrodimerization of toluene with a subsequent catalytic conversion of the resulting dehydrodimerization products to styrene at a temperature within the range of from 300° to 600° C. The conversion of the dehydrodimerization products is conducted in the presence of ethylene with the use of a catalyst consisting of the following components, percent by weight:

| | |
|---|---|
| chromium oxide | 1.5 to 5.2 |
| tungsten oxide | 4.0 to 6.1 |
| oxide of an alkali metal | 0.1 to 0.7 |
| silica or alumosilicate | the balance. |

DETAILED DESCRIPTION OF THE INVENTION

The method for preparing styrene according to the present invention is performed in the following manner.

Toluene is subjected to dehydrodimerization in the presence of oxygen (air) on a catalyst containing bismuth oxide at a temperature of from 400° to 600° C.

The dehydrodimerization product consists by more than 80% of dibenzyl, the balance being stilbene.

The mixture of dibenzyl and stilbene is subjected to conversion with ethylene in the presence of the above-mentioned catalyst consisting of chromium oxide, tungsten oxide, an oxide of an alkali metal and silica or alumosilicate and possessing dehydrogenating and disproportioning properties. Conversion is conducted at an elevated temperature (300° to 600° C.) and under atmospheric or overatmospheric pressure of up to 5 atm.g. Proportions of the dehydrodimerization products of toluene and ethylene may be varied within a wide range. Technologically optimal is a ratio within the interval of from 1:3 to 1:10, which is associated with recycle of ethylene.

The conversion catalyst is produced by depositing oxides of chromium, tungsten and an alkali metal in an appropriate ratio onto a carrier such as silica or alumosilicate. The best results are obtained with the following proportions of the components, percent by weight:

| | |
|---|---|
| chromium oxide | 1.5 to 5.2 |
| tungsten oxide | 4.0 to 6.1 |
| oxide of an alkali metal | 0.1 to 0.7 |
| silica or alumosilicate | the balance. |

The yield of styrene in the method according to the present invention comprises 78 to 80% by weight of styrene per the converted products of dehydrodimerization of toluene and ethylene.

The method according to the present invention does not imply separation or hydrogenation of stilbene and, thereby, it involves a lesser number of process stages, i.e. has a more simplified technology.

For a better understanding of the present invention, given hereinbelow are some specific examples illustrating the method for preparing styrene.

EXAMPLE 1

92 g of toluene are passed, in a mixture with air at a molar ratio between oxygen and toluene of 0.8:1, at a temperature of 490° C. and contact time of 1.2 sec, over a catalyst containing 37% by weight of bismuth oxide on corundum. The resulting liquid product contains 0.8 g (0.9% by weight) of benzene, 2.8 g (3.1% by weight) of a mixture of dibenzyl and stilbene, the balance being represented by toluene.

The mixture of dibenzyl and stilbene containing at least 87% by weight of dibenzyl is separated by rectification.

100 g of the mixture of products of toluene dehydrodimerization produced under the above-mentioned conditions and 92 g of ethylene are passed at a temperature of 490° C. at the space velocity of 200 $hr^{-1}$ over a catalyst containing 5.2% by weight of $Cr_2O_3$, 6.1% by weight of $WO_3$, 0.15% by weight of $Na_2O$ on silica.

As a result of the conversion there are obtained (g): $H_2$—0.1; $CH_4$—0.4; $C_2H_4$—71.7; $C_2H_6$—8.0; $C_2$—$C_5$ hydrocarbons—1.8; benzene 0.8; toluene—7—1; ethylbenzene—9.2; styrene 72.4; stilbene—0.6; dibenzyl—17.6; high-boiling products—0.8.

Conversion of dibenzyl is 82.4%.

The yield of styrene as calculated for the converted stilbene, dibenzyl and ethylene is 72% by weight.

From the reaction products a 99.9% purity styrene is recovered by rectification.

EXAMPLE 2

92 g of toluene are passed through the reactor at a temperature of 900° C. and contact time of 0.005 sec. The pyrolysis products contain hydrogen and light hydrocarbons in an amount of 0.02 g, benzene 0.04 g, toluene 90.34 g, xylenes 0.16 g, dibenzyl 1.41 g, high-boiling hydrocarbons 0.03 g. Conversion of toluene is 1.8%, selectivity of the formation of dibenzyl is 84.7% by weight.

70 g of dibenzyl produced under the above-described conditions and 158 g of ethylene are passed at a space velocity of 180 hr$^{-1}$ at a temperature of 325° C. over a catalyst consisting of 1.5% by weight of $Cr_2O_3$, 4.0% by weight of $WO_3$, 0.7% by weight of $Na_2O$, 8.8% by weight of $Al_2O_3$ and 85% by weight of $SiO_2$.

As a result of conversion there are obtained (g): hydrogen—0.1; $CH_4$—0.2; $C_2H_4$—137.8; $C_2H_6$—6.4; $C_3$–$C_5$ hydrocarbons—0.6; benzene 0.4, toluene 1.2; ethylbenzene—4.2; styrene 50.1; stilbene—0.2; dibenzyl—26.5; high-boiling products—0.3.

Conversion of dibenzyl is 62.0%.

The yield of styrene as calculated for the converted dibenzyl and ethylene is 80.0% by weight.

Styrene with the basic compound content of 99.9% by weight is separated from the reaction products by rectification.

EXAMPLE 3

A mixture of 74 g of dibenzyl and 26 g of stilbene prepared upon dehydrodimerization of toluene under the conditions described in the foregoing Example 1 is mixed with 136 g of ethylene and passed over a catalyst consisting of 3.3% by weight of $Cr_2O_3$, 4.5% by weight of $WO_3$, 0.7% by weight of $K_2O$; 33.3% by weight of $Al_2O_3$; 58.2% by weight of $SiO_2$, at a temperature of 569° C. at the space velocity of 165 hr$^{-1}$.

As a result of the conversion there are obtained, (g): hydrogen—0.1; $C_2H_4$—116.2; $CH_4$—0.2; $C_2H_6$—5.4; $C_3$—$C_5$ hydrocarbons—0.3; benzene—1.2; toluene—4.2; ethylbenzene—6.8; styrene—76.6; stilbene—0.9; dibenzyl—20.9; high-boiling products—3.2.

Conversion of the mixture of dibenzyl and stilbene is 78.2%.

The yield of styrene as calculated for the converted mixture of dibenzyl, stilbene and ethylene is 78.2% by weight.

Styrene with the principal compound content of 99.9% is recovered from the conversion products rectification.

What is claimed is:

1. A method for preparing styrene which comprises dehydrodimerization of toluene with a subsequent catalytic conversion of the resulting dehydrodimerization products to styrene at a temperature ranging from 300° to 600° C. in the presence of ethylene using a catalyst consisting of the following components, percent by weight:

| | |
|---|---|
| chromium oxide | 1.5 to 5.2 |
| tungsten oxide | 4.0 to 6.1 |
| an oxide of an alkali metal | 0.1 to 0.7 | a carrier selected from the group consisting of silica and alumosilicate the balance.

* * * * *